(12) United States Patent
Mehta et al.

(10) Patent No.: US 8,202,542 B1
(45) Date of Patent: Jun. 19, 2012

(54) ABUSE RESISTANT OPIOID DRUG-ION EXCHANGE RESIN COMPLEXES HAVING HYBRID COATINGS

(75) Inventors: Ketan Mehta, Cranbury, NJ (US);
Yu-Hsing Tu, West Windsor, NJ (US);
Alivia Chaudhuri, Cranbury, NJ (US);
Ashok Perumal, Edison, NJ (US)

(73) Assignee: Tris Pharma, Monmouth Junction, NJ (US)

( * ) Notice: Subject to any disclaimer, the term of this patent is extended or adjusted under 35 U.S.C. 154(b) by 760 days.

(21) Appl. No.: 12/154,970

(22) Filed: May 28, 2008

Related U.S. Application Data

(60) Provisional application No. 60/941,169, filed on May 31, 2007.

(51) Int. Cl.
*A61K 9/14* (2006.01)
*A61K 9/20* (2006.01)
*A61K 9/48* (2006.01)

(52) U.S. Cl. ........ 424/489; 424/451; 424/452; 424/464; 424/465

(58) Field of Classification Search .................. None
See application file for complete search history.

(56) References Cited

U.S. PATENT DOCUMENTS

| | | |
|---|---|---|
| 4,221,778 A | 9/1980 | Raghunathan |
| 4,861,598 A | 8/1989 | Oshlack |
| 4,996,047 A | 2/1991 | Kelleher et al. |
| 5,266,331 A | 11/1993 | Oshlack et al. |
| 5,508,042 A | 4/1996 | Oshlack et al. |
| 5,549,912 A | 8/1996 | Oshlack et al. |
| 5,656,295 A | 8/1997 | Oshlack et al. |
| 5,672,360 A | 9/1997 | Sackler et al. |
| 5,733,575 A | 3/1998 | Mehra et al. |
| 6,001,392 A | 12/1999 | Wen et al. |
| 6,555,127 B2 | 4/2003 | Steiner |
| 6,756,057 B2 | 6/2004 | Storm et al. |
| 2003/0099711 A1 | 5/2003 | Meadows et al. |
| 2004/0028729 A1* | 2/2004 | Shojaei et al. ............... 424/452 |
| 2004/0126428 A1 | 7/2004 | Hughes et al. |
| 2005/0163856 A1 | 7/2005 | Maloney et al. |
| 2005/0265955 A1 | 12/2005 | Raman et al. |
| 2006/0115529 A1 | 6/2006 | Jeong et al. |
| 2007/0215511 A1 | 9/2007 | Mehta et al. |

FOREIGN PATENT DOCUMENTS

| | | |
|---|---|---|
| WO | WO 01/70194 A1 | 9/2001 |
| WO | WO 2005/117843 A2 | 12/2005 |
| WO | WO 2005117843 A2 * | 12/2005 |
| WO | WO 2006/101536 A1 | 9/2006 |
| WO | WO 2006/124898 A1 | 11/2006 |
| WO | WO 2007/109104 A3 | 9/2007 |
| WO | WO 2007109104 A3 * | 12/2007 |

OTHER PUBLICATIONS

Kadian® (morphine sulfate extended-release capsules), Product Literature, Revised Oct. 2006.
Avinza® (morphine sulfate extended-release capsules), Product Literature, Prescribing Information, Apr. 2008.
Oxycontin® (Oxycodone HCI Controlled-Release) Tablets, pp. 1-29, Product Literature, Purdue Pharma L.P. Stamford, CT 06901-3431, Jan. 15, 2007.

* cited by examiner

*Primary Examiner* — Susan Tran
(74) *Attorney, Agent, or Firm* — Cathy A Kodroff; Howson & Howson LLP; Egon Berg

(57) ABSTRACT

A sustained release formulation for opioid drugs is described. The formulation contains an opioid-ion exchange resin complex having a hybrid coating. The hybrid coating contains a cured polyvinylacetate polymer and a pH-dependent enteric coating layer mixed therein. Also provided are methods of making and using same.

25 Claims, No Drawings

ABUSE RESISTANT OPIOID DRUG-ION EXCHANGE RESIN COMPLEXES HAVING HYBRID COATINGS

CROSS-REFERENCE TO RELATED APPLICATIONS

This application claims the benefit under 35 USC 119(e) of U.S. Provisional patent application No. 60/941,169, filed May 31, 2007.

BACKGROUND OF THE INVENTION

Opioids are commonly prescribed because of their effective analgesic, or pain-relieving, properties. Medications that fall within this class, referred to as prescription narcotics, include morphine sulfate (e.g., Kadian®, Avinza™), codeine salts, oxycodone HCl (e.g., OxyContin™, Percodan™, Percocet™), and related drugs. For example, OxyContin™ tablets are presently commercially available in 10, 20, 40, 80, and 160 milligrams forms. Morphine, for example, is often used before and after surgical procedures to alleviate severe pain. Codeine, on the other hand, is often prescribed for mild pain. In addition to their pain-relieving properties, some of these drugs can be used to relieve coughs and diarrhea. Codeine and diphenoxylate (Lomotil™) are examples of such drugs. However, opioid drugs are at times associated with side effects including, e.g., stomach upset and other gastrointestinal effects. Further, because of the sometimes addictive properties of these drugs and the euphoria which can be associated with taking them, including through routes other than those prescribed, these opioid drugs are particular susceptible to abuse.

In order to reduce some of the gastrointestinal effects of these drugs, sustained release dosage forms have been described. For example, a sustained-release dosage form for morphine sulfate has been described [WO 2006/124898], in which a morphine sulfate core is coated with a matrix polymer insoluble at pH 1 to 7.5, an enteric polymer soluble at pH 6 to 7.5, and an acid soluble polymer which is soluble at pH 1 to 4, and having a ratio of acid soluble polymer to enteric polymer of 1.45:1 to 2.5:1 on a weight basis. Certain sustained release formulations are commercially available under the trademark Kadian® and are currently available in 20, 30, 50, 60 and 100 mg capsules.

Attempts to reduce abuse of opioid by pharmacological methods have been made. One such attempt involves including an "opioid antagonist" along with the opioid "agonist". These antagonists cannot be easily extracted from the agonist and will cause an aversive effect in a physically dependent patient. However, these antagonists may have other side effects which may be disadvantageous.

One attempt to reduce opioid abuse and avoid the use of an agonist-antagonist combination has been described in US 2005/0163856A1, published Jul. 28, 2005. This patent application describes an oxycodone formulation designed to provide a pH independent release rate with a peak plasma level between 5-6 hours after administration. The formulation provides an oxycodone mixed with 40-65 wt % matrix forming polymer and 5 to 15 wt % of an ion exchange resin.

Ion exchange resins coated with a diffusion barrier coating have been described for the preparation of sustained release systems for preparing sustained release formulations. See, US-2006-0115529; WO 2006/101536; WO 2005/117843; US-2005-0265955 A1; WO 01/070194; U.S. Pat. Nos. 4,221,778, 4,996,047, and 4,861,598.

For example, U.S. Pat. No. 6,001,392 granted Dec. 14, 1999 describes certain acrylate based (e.g., EUDRAGIT polymer system) and ethyl cellulose (e.g., SURELEASE, AQUACOAT) polymers for coating a drug-ion exchange resin complex using either a solvent or aqueous based coating to achieve sustained release of the drug from the drug-ion exchange resin complex. There appears to be no meaningful data regarding the integrity of the coating film. Further, there is no data in the '392 patent of prolonged release of the drug from the coated drug-ion exchange resin complex beyond about 12 hours. There have been literature-reported drawbacks of using ethyl cellulose based aqueous dispersions as coatings for drug-ion exchange resin complexes.

Enteric coatings have been described as delayed release polymers for providing an initial delay in drug release. See, e.g., U.S. Pat. No. 6,756,057 for amoxicillin and U.S. Pat. No. 6,555,127 for methylphenidate. Enteric coatings are also used for protecting the body from drugs which cause gastric irritation (e.g., naproxen which is commercially available as enteric coated tablet and capsule formulations).

US-2006-0115529 and WO 2006/101536 describe the use of film coatings for a fast melt tablet containing ion exchange resin complex particles mixed with a dry binder and bulk diluent. One suitable coating described is the KOLLICOAT SR30D polymer system. Optional use of an enteric coat which is insoluble in acidic pH and soluble in basic pH is described.

US-2004-0126428 describes a product which is described as being abuse resistant. This product contains a core comprising a resonate of an opioid formed from the drug (e.g., morphine sulfate) and an ion exchange resin. A multi-component coating may also applied to the core, which contains (a) from 1 to 85% by weight of a matrix polymer which is insoluble at a pH of from 1 to 7.5 and contributes to the control of the rate of release of the active ingredient in the stomach and intestines; (b) from 1 to 30% of an enteric polymer which is substantially insoluble at a pH of from 1 to 4, sufficient to delay the release of the active ingredient in the stomach, but which is soluble at a pH of from 6 to 7.5 so as not to substantially delay release in the intestines; (c) from 1 to 60% of a compound soluble at a pH of from 1 to 4.

US 2003-0099711 A1 describes using an ethyl cellulose polymer in an aqueous based coating system as a barrier coating. This publication further describes use of an optional enteric coating over the barrier coating to delay the drug release.

Opioid drug formulations which provide a desired sustained release profile without requiring an agonist-antagonist combination to reduce abuse are desirable from a commercial drug perspective.

SUMMARY OF THE INVENTION

The present invention provides a modified release tablet formulation of an opioid drug bound to an ion exchange resin, coated with a hybrid coating comprising a barrier coating containing a polyvinyl acetate polymer and a plasticizer and an enteric polymer mixed therewith.

Advantageously, the combination of sustained release provided by the complexation of the opioid drug with the ion exchange resin and the hybrid layer coating comprising the barrier coating component and the enteric coating component, provide a desired modified release profile while also providing favorable abuse resistance properties.

In one embodiment, the drug-ion exchange resin complex further comprises a solvating agent or a release retardant.

In a further embodiment, the invention provides a solid dose modified release morphine formulation. This formulation may be a tablet or a capsule containing granules of the invention and contains a pharmaceutically effective amount of morphine bound to a pharmaceutically acceptable cationic exchange resin complex. The complex is provided with a cured hybrid modified release coating directly thereon. The hybrid coating comprises a single cured layer comprising a uniform mixture of a barrier forming component containing at least a polyinylacetate (PVA) polymer system and a plasticizer and enteric coating forming component preferably containing at least a PVA-phthalate and at least one plasticizer.

The invention further provides a method of administering an opioid drug (e.g., morphine) for a sustained period, the method comprising administering a formulation of an opioid drug bound to an ion exchange resin, coated with a hybrid coating as described herein.

Other aspects and advantages of the invention will be readily apparent from the following detailed description.

DETAILED DESCRIPTION OF THE INVENTION

The present invention provides an opioid drug-ion exchange resin complex having a cured hybrid coating composed of a water-insoluble, water-permeable based diffusion barrier coating component and an enteric coating component. This cured, hybrid coated opioid-drug ion exchange resin complex of the invention provides desirable modified release properties while also providing desired abuse resistance.

The "barrier coating component" is a polyvinylacetate-based polymeric system, containing a plasticizer. Polyvinyl acetate, due to its high tensile strength in the presence of a plasticizer(s), provides a flexible coating film for use as the water-permeable diffusion barrier coating that maintains its film integrity even when subjected to severe physical force and stress such as during a compression step in a tabletting machine or the grinding action of a coffee beans grinder, mill, etc. As described herein, this material remains substantially non-tacky and process-friendly with the addition of a plasticizer during the coating operation in a Wurster fluid bed or other coating operation and do not cause agglomeration during the coating of very fine particles of drug-ion exchange resins. Agglomeration (sometimes termed "caking" or "brick formation") during a coating operation may otherwise impede the air flow, destroy flow pattern, and/or clog the spray nozzle, thereby increasing the possibility of an imperfect and uneven coating of the drug-ion exchange resin particles.

As used herein, the term "enteric coat component" refers to a polymer system having pH-dependent solubility. More particularly, an enteric coat component used in the present invention is insoluble in an aqueous system at acidic pH, e.g., in the range typically found in the stomach, but soluble at higher pH such as are found in the lower gastrointestinal tract. In one embodiment, the enteric coat component is insoluble at pH 1 to about 5.5 and soluble at a pH above about 5.5 in an aqueous system (e.g., gastric juices). Further, the enteric polymer selected for use in the invention is compatible with the barrier coating component of the hybrid coat. More particularly, the enteric coating polymer(s) is non-reactive with the barrier coating, i.e., does not form a gel or gel-like substance, and allows uniform application of the hybrid coating to the resin. For example, in one embodiment, the barrier coating component is a polyvinylacetate-based polymeric system; the inventors found that a mixture of this polymeric system with a water insoluble methacrylic acid:acrylic acid ethylester 1:1 copolymer enteric coating polymers [commercially available as Eudragit™ L30 D55] reacted to form a gel-like substance which could not be satisfactorily applied as a coating material. In another example, another methacrylic acid: ethylacrylic acid copolymer [commercially available as a 30% dispersion under the name Eudragit L100 55] when mixed with the barrier coating component was found to cause undesirable "clumping" or clogging of the coating apparatus when mixed with the barrier coating component and prevented uniform application of the hybrid coating.

One particularly suitable enteric polymer is a polyvinylacetate phthalate (PVAP) based system, which the inventors found to combine and mix well with the polyinylacetate-based barrier coating. One such enteric polymer system is available commercially as SURETERIC™, which is described in U.S. Pat. No. 5,733,575 (see, particularly example 1), the disclosure of which is incorporated by reference herein. The '575 patent describes an enteric polymer system which, in one embodiment, is formed by the mixture of PVAP with a liquid plasticizer, a solid plasticizer, a detackifier and a lubricant. Suitably, the enteric polymer system also contains an alkalizing agent, a viscosity modifier, an anticaking agent, and may include an anti-foam solution to prevent foaming during preparation. The final enteric polymer solution is passed through a 60 mesh screen. The '575 patent describes the use of titanized PVAP or jet milled PVAP. In Example 1, titanized PVAP is utilized, which is described earlier in the document as having 10% titanium dioxide mixed into the PVAP while it is being made. The SURETERIC™ enteric dry powder composition is prepared as described in Example 1 of the '575 patent, by mixing the liquid plasticizer Citroflex triethylcitrate into titanized PVAP, the alkalizing agent sodium bicarbonate, the solid plasticizer polyethylene glycol 3350, the lubricant stearic acid, the viscosity modifier sodium alginate, and Cabosil Eh5 silica (anticaking), and mixing in water with an antifoaming solution. Other suitable PVAP systems useful in the invention may be designed taking into consideration this information and the desirable enteric polymer system properties described herein.

Advantageously, the hybrid coating material of the present invention is sufficiently flexible that it can withstand the amount of pressure applied during compression of the coated drug-ion exchange resin particles into tablet or granular form. Further, following oral delivery and after passing through the stomach and into the higher pH level of the lower gastrointestinal tract, the pH-dependent, water-soluble enteric polymer (e.g., PVAP based system) begins to dissolve. Thus, the enteric polymer component of the hybrid coating serves as a pH-dependent pore-former which provides initial delayed release to the dosage unit, whereas the water permeable barrier coating polymer system (polyvinyl acetate-based system) continues to control release. These solid oral dose units are believed to function in a manner similar to a multiparticulate system; more particularly, the tablet or capsule disintegrates in the stomach to release the particles (granules), which release active drug evenly and reduce variability in the release profile.

Thus, the drug release pattern from the compositions of the present invention is controlled or modified by combining at least one opioid drug (e.g., morphine sulfate) and an ion exchange resin (e.g., a cationic resin) to form the drug-resin complex prior to the application of the hybrid water-permeable diffusion barrier coating-enteric coating layer.

Optionally, other water-insoluble polymers may be included in the drug-ion exchange resin complex, including a single polymer or mixtures thereof, such as may be selected from polymers of ethyl cellulose, polyvinyl acetate, cellulose acetate, polymers such as cellulose phthalate, acrylic based polymers and copolymers (such as, for example, those available under EUDRAGIT brand name) or any combination of such insoluble polymers or polymer systems herein defined as a "release retardant". The drug-ion exchange resin complex with or without a "release retardant" may be formulated to achieve the desired length of time of drug release rate from such drug-ion exchange resin complexes. Such coating systems could be further customized by the incorporation of individual or a combination of hydrophilic or lipophilic plasticizers with a dispersion or suspension containing the barrier coating polymer. Such plasticizers include, e.g., propylene glycol, polyethylene glycol, triacetin, triethyl citrate, dibutyl sebacate, vegetable oil, lipids, etc.

As used herein, the term "modified release" refers to compositions of the invention which are characterized by having a drug release from a drug-ion exchange complex of the invention over a period of at least about 12 hours, and preferably up to about 24 hours. The release profile may be assessed using in vitro dissolution assays known to those of skill in the art [e.g., USP basket method or Paddle Method, or channel flow method]. The release profile can be assessed in vivo (e.g., for bioequivalence determinations), using plasma concentrations to assess maximum concentration (Cmax) and area under the curve (AUC). Such assays are well known to those of skill in the art.

For example, a modified release composition of the invention can be tailored to at least essentially match the in vivo release profile of a commercially available prescription opioid modified release composition. In one embodiment, the composition of the invention is tailored to meet the in vivo release profile of a 12 hour or 24 hour product, e.g., such as the sustained release morphine sulfate KADIAN® morphine sulfate capsules, Avinza® morphine sulfate, MS CONTIN® morphine sulfate or a OxyCONTIN® oxycodone product [in vivo release profiles published in product literature, also available from Kadian® web cite and the Physician's Desk Reference]. See, also, U.S. Pat. Nos. 5,508,042; 5,266,331; 5,549,912; 5,656,295, for a description of the release profile of the Kadian® release profile. See, also, U.S. Pat. No. 5,672, 360.

In one embodiment, a tablet prepared from the hybrid coated ion exchange resin complex of the invention provides an in vitro dissolution rate of about 5 to about 20% in 1 hour, about 30% to about 50% in 2 hours, about 70% to about 85% in 4 hours, and more than 90% in 12 hours, e.g., as measured by the USP Paddle Method. A capsule containing granules can be designed to provide a similar release rate. The product is expected to provide an in vivo therapeutic effect lasting for at least 12 up to about 24 hours.

The term "modified release" may include, e.g., compositions which are extended release formulations (also termed "prolonged release formulation"), sustained release formulations, certain pulse delivery systems, or delay release formulations.

The hybrid coated opioid-ion exchange resin complexes of the invention and formulations (Example 2) containing the complex provide desirable abuse resistance properties. Certain commercial opioid products, such as Kadian® morphine sulfate, report in its product literature that the capsules are to be swallowed whole or sprinkled in applesauce. The pellets in the Kadian® morphine sulfate capsule are not to be chewed, crushed or dissolved, all of which would lead to rapid release and absorption of morphine. The OxyContin® oxycodone product literature contains a similar warning for its oxycodone product. The hybrid coated opioid-ion exchange resin complex of the invention is designed to provide an advantage in delaying release of active over products which could provide an almost immediate release of such active opioid ingredient upon such abuse of such product.

Further properties of the hybrid coating system of the present invention are discussed below.

As used herein in reference to numeric values provided herein, the term "about" may indicate a variability of as much as 10%.

A detailed description of the components of the compositions of the present invention follows.

Opioid Drugs

The formulations of the invention are particularly well suited for oral dosage units containing opioid drugs having abuse potential. In one embodiment, these oral dosage units are solid dosage units. However, these formulations are adaptable to other types of dosage units (e.g., suspension, etc) and other active components.

In one embodiment, the opioid drugs are used in the treatment of respiratory tract disorders such as, for example, antiitussive expectorants such as dihydrocodeine phosphate, codeine phosphate, and noscapine hydrochloride. In another embodiment, the opioid drugs are analgesics drugs such as hydrocodone, morphine, hydromorphone, oxycodone, codeine, levorphanol, meperidine, methadone, oxymorphone, buprenorphine, fentanyl and derivatives thereof, dipipanone, tramadol, etorphine, dihydroetorphine, butorphanol, levorphanol, or salts thereof or mixtures thereof. In one embodiment, the opioid is morphine, oxycodone, hydrocodone, or a salt thereof. In one embodiment, a morphine salt is morphine sulfate; an oxycodone salt is oxycodone HCl; and a codeine salt is codeine sulfate or phosphate.

The pharmaceutically acceptable salts include, but are not limited to, inorganic acid salts such as hydrochloride, hydrobromide, sulfate, phosphate and the like; organic acid salts such as formate, acetate, trifluoroacetate, maleate, tartrate and the like; sulfonates such as methanesulfonate, benzenesulfonate, p-toluenesulfonate, and the like; amino acid salts such as arginate, asparaginate, glutamate and the like. Other suitable salts will be readily apparent to one of skill in the art.

In certain embodiments, the amount of the opioid drug in the composition may be about 1 mg to 250 mg. In another embodiment, the amount of the opioid drug in the composition is about 5 mg to about 200 mg. In still another embodiment, the amount of the opioid drug in the composition is about 10 mg to about 150 mg. The preceding list is not intended to be exclusive. In some embodiments, the composition of the invention is designed to provide a release profile similar to a commercially available product. In such an instance, the present invention provides an equivalent amount of active opioid to the commercially available product based on weight. In another embodiment, the present invention provides an amount of active opioid bioequivalent to the commercially available product, i.e., provides a finished formulation having an in vivo release profile similar that of the commercial product. This can be readily determined by taking into consideration the molecular weight of the free base of the opioid drug bound to the resin, as compared to the compound in the commercial product, and further taking into consideration the percentage of active drug loaded on the resin. These calculations are well within the skill of one in the art.

Ion-Exchange Resin

Ion-exchange resins suitable for use in these preparations are water-insoluble and comprise a preferably pharmacologically inert organic and/or inorganic matrix containing functional groups that are ionic or capable of being ionized under the appropriate conditions of pH. Typically the size of the ion-exchange particles is from about 10 microns to about 420 microns, preferably the particle size is within the range of about 40 microns to about 250 microns for solid dosage forms, e.g., tablets and granules placed in capsules. Particle sizes substantially below the lower limit are generally difficult to handle in all steps of the processing. Generally, uncoated drug-ion exchange resin particles of the invention will tend to be at the lower end of this range, whereas coated drug-ion exchange resin particles of the invention will tend to be at the higher end of this range. However, both uncoated and coated drug-ion exchange resin particles may be designed within this size range. For additional discussion of ion exchange resins, see, e.g., co-pending US Patent Publication No. 2007-0215511 A1, published Sep. 20, 2007, [application Ser. No. 11/724,966, filed Mar. 15, 2007, entitled "Modified release formulations containing drug-ion exchange resin complexes"] and its international counterpart WO 2007/109104, published Sep. 27, 2007, which are incorporated by reference.

A suitable ion exchange resin is selected depending upon the charge of the active opioid or its salt. For example, cation exchange resins are well suited for use with drugs and other molecules having a cationic functionality, including, e.g., oxycodone, morphine, hydrocodone, oxymorphone, and hydromorphone, as well as prodrugs, salts, isomers, polymorphs, and solvates thereof. Cationic exchange resins have been described in the art and also commercially available. Examples of commercially available cationic resins include, without limitation, Dow XYS-40010.00 and Dow XYS-40013.00 (The Dow Chemical Company), Amberlite IRP-69 (an insoluble, strongly acidic, sodium polystyrene cation exchange resin), Amberlite IRP-64 (weekly acidic), Amberlite IRP-120 (Rohm and Haas), Amberlite IRP-88 (weakly acidic). Amberlite IRP-69 (Rohm and Haas) is sulfonated polymers composed of polystyrene crosslinked with 8% of divinylbenzene, with an ion exchange capacity of about 4.5 to 5.5 meq/g of dry resin. It consists of irregularly shaped particles with a size range of 47 to 149 microns. A series of cationic resins are also available from DOW Chemical as the DOWEX™50WX series (Dow Chemical Company). There are mainly four products with different particle size distribution: cut-off mesh size is US Sieve No. 50 (300 microns) in the case of Dowex™ 50WX2-50, 100 (150 microns) in Dowex™ 50WX2-100, 200 (75 microns) in Dowex™ 50WX2-200, and 400 (38 microns) in Dowex™ 50WX2-400. Crosslinking is another important factor, which can influence physical properties, equilibrium conditions, drug loading, and drug release profiles. Resins of various degrees of permeability are dependent on the divinylbenzene content, which was described as the degree of resin crosslinkage and the number after X is the percentage of divinylbenzene in the resin polymer. For example, Dowex™ 50WX2-50 contains 2% divinylbenzene with particle size is bigger than 50 mesh. Total exchange capacity of 2, 4 and 8% crosslinkage resins are 0.6, 1.1 and 1.7 meq/ml, respectively. Still other ion exchange resins are available from Sigma-Aldrich.

Both strongly acidic and weakly acidic resins (e.g., cationic resins) are commercially available and can be selected for use. However, it will be understood that the strength of the bond between the opioid drug and the resin will be affected by whether the resin is strongly acidic or weakly acidic. More particularly, a stronger bond will typically be formed by the strongly acidic resin and thus, drugs loaded thereon will have a slower release profile than those loaded on a weakly acidic resin. Thus, one of skill in the art can select the desired type of resin to achieve a desired release profile, further taking into consideration such factors as the use of a release retardant, the thickness of the hybrid coating, and the ratio of barrier coating component to enteric coating component.

Other suitable resins can be selected by one of skill in the art, taking into consideration the charge of the free base or salt form of a desired opioid drug.

The selected ion-exchange resins may be further treated by the manufacturer or the purchaser to maximize the safety for pharmaceutical use or for improved performance of the compositions. Impurities present in the resins may be removed or neutralized by the use of common chelating agents, antioxidants, preservatives such as disodium edetate, sodium bisulfate, and so on, by incorporating them at any stage of preparation either before complexation or during complexation or thereafter. These impurities along with their chelating agent to which they have bound may be removed before further treatment of the ion exchange resin with a release retardant and diffusion barrier coating.

Opioid Drug-Ion Exchange Resin Complexes

Binding of the selected opioid drug or a combination of drugs including at least one opioid drug to the ion exchange resin can be accomplished using methods known in the art. See, e.g., co-pending US Patent Publication No. 2007-0215511 A1, published Sep. 20, 2007, [application Ser. No. 11/724,966, filed Mar. 15, 2007, entitled "Modified release formulations containing drug-ion exchange resin complexes"] and its international counterpart WO 2007/109104, published Sep. 27, 2007, and the documents cited therein, incorporated by reference.

The amount of drug that can be loaded onto a resin will typically range from about 1% to about 75% by weight of the drug-ion exchange resin particles. A skilled artisan with limited experimentation can determine the optimum loading for any drug resin complex, taking into such consideration as the desired amount of active drug and the desired size of the final dose formulation. For example, to reduce the size of a formulation or to increase the amount of active drug, a higher loading percentage may be used. Conversely, where a lesser amount of active drug is desired, a loading percentage at the lower end of this range may be provided. In one embodiment, loading of about 10% to about 40% by weight, more desirably, about 15% to about 30% by weight, of the drug-ion exchange resin particles can be employed. Typical loadings of about 25% by weight of the drug-ion exchange resin particles can be advantageously employed.

Thus, in one aspect, the invention provides drug-ion exchange resin complexes comprising an opioid drug loaded in an ion exchange resin as described herein. The drugs and ion exchange resins may be readily selected from amongst those drugs and resins described herein. The invention further provides drug-ion exchange resin matrixes defined as follows.

Release Retardants

The drug release rate from the compositions of the present invention may be further prolonged or modified by treating the drug-ion exchange resin complex prior to the application of the hybrid coating described herein, with a release retardant which is a water-insoluble polymer or a combination of a water-insoluble polymers.

Advantageously, the release retardant does not form a separate layer on the drug-ion exchange resin complex, but forms a matrix therewith. Examples of suitable release retardants include, for example, a polyvinyl acetate polymer or a mixture of polymers containing same (e.g., KOLLICOAT SR 30D), cellulose acetates, ethylcellulose polymers (e.g., AQUACOAT™ ECD-30 or SURELEASE™), acrylic based polymers or copolymers (e.g., represented by the EUDRAGIT family of acrylic resins), cellulose phthalate, or any combination of such water-insoluble polymers or polymer systems, all herein defined as "release retardants". These retardants when used may further prolong or alter the release of the drug from the coated drug-ion exchange resin complex and maximize attaining the desired release profile. Further, use of a release retardant permits in some cases lowering the amount of coating thickness needed to attain a prolonged drug release of up to 24 hours. These retardants can be used in either substantially pure form or as a commercial preparation obtained from a vendor. The preferred release retardant is a polyvinyl acetate polymer system, e.g. the KOLLICOAT SR30D system, as described herein or an acrylic polymer from the EUDRAGIT family. Examples of suitable acrylic polymers from the EUDRAGIT family may include, e.g., a copolymer comprising ethyl acrylate and methyl methacrylate (e.g., EUDRAGIT NE-30D), or EUDRAGIT RS, RL30D, RL100, or NE, which are largely pH-independent polymers; less desirable, certain pH-dependent members of the EUDRAGIT polymer family, e.g., the L, S, and E, polymers may be selected].

The quantity of polymer that is added as a release retardant typically ranges from about 3% to about 30% or more by weight of the uncoated drug-ion exchange resin particles. More preferably the release retardant, if used, is in the range from about 5% to about 20% and most preferably in the range of about 10% to about 15% by weight of the uncoated drug-ion exchange resin particles, depending on the nature of the drug-ion exchange resin complex and the desired release profile of the medicinal agent(s). In one embodiment, the composition of the invention is designed to match the in vivo release profile of a commercially available drug(s).

These release retardants can be added during the formation of the drug-ion exchange resin complex either in the beginning, during the middle, or after substantial amount of complex formation has taken place. In the more preferred embodiment, the retardant is added after the formation of drug-ion exchange resin complex. Upon mixing, the drug-ion exchange resin complex particles with the release retardant, the mixture is dried and milled appropriately. In some cases, the milling may be carried out before the complete drying of the complex and then again further drying followed by milling to obtain the desired complex characteristics.

The release rate of the present aqueous based hybrid coating of the invention which are designed to provide finished dosage orally ingestible pharmaceutical compositions such as tablets, capsules, etc. are tailored to provide the desired drug release profile over a period of about 8 to 24 hours, and preferably 12 to 24 hours.

This programmable release rate may be controlled by the hybrid coating thickness and optionally, the use of "a release retardant" component as described above, added to the drug-ion exchange resin complex to form a fine particulate matrix prior to the polymer film coating step. The release retardant is preferably a water insoluble polymer as previously described such as a PVA dispersion which has the same or similar composition of solids as the preferred aqueous based film forming coating polymer dispersion described herein used in the coating step or an acrylic based polymer available commercially under the EUDRAGIT™ brand name, manufactured by Degussa (previously manufactured by Rohm Pharma Polymers). The properties of different EUDRAGIT™ compositions commercially available are described in literature from Degussa or Rohm Pharma and are also described in U.S. Pat. No. 6,419,960 (column 10-11), the disclosure of which is incorporated herein by reference. Other water insoluble polymers include those listed in column 10, lines 41-53 of U.S. Pat. No. 6,419,960 the disclosure of which is incorporated herein by reference.

Another embodiment is the use of an impregnating (solvating) agent as a release retardant incorporated into the pharmaceutically acceptable drug ion-exchange resin complex prior to addition of the aqueous based coating. This impregnating (solvating) agent is a hydrophilic (water soluble) agent exemplified by those materials described for example in U.S. Pat. No. 4,221,778 and published US patent application Publication No. US 2003/009971 A1, the disclosures of which are incorporated herein by reference. Specific examples of suitable impregnating agents include propylene glycol, polyethylene glycol, polyvinyl alcohol, polyvinyl pyrrolidone (e.g., KOLLIDON™ K30) mannitol, methyl cellulose, hydroxypropyl methylcellulose, hydroxypropyl cellulose, and sorbitol.

In one embodiment, the coated drug-ion exchange resin complex particles are mixed in the presence of a granulating agent, to aid in providing particles with a relatively even particle size range. The granulating agent can be one or more substances that do not adversely react with the other components of the complex and/or the active ingredient(s). Suitable granulating agents include the release retardant, solvating agent, sweetener(s) and the like.

Suitably, the resulting drug-ion exchange resin complexes are of a size in the range of about 20 microns to 420 microns, which are predominantly in the range of about 40 microns to about 250 microns, with particles up to about 420 micron being used for solid dosage forms, e.g., tablets and granules in capsules. It has been found that particles above about 420 microns have a somewhat undesirable mouth feel following administration.

Coating System

Suitably, the present invention provides a hybrid coating is a cured coating composed of a water permeable, water insoluble barrier coating component comprising at least a polyvinyl acetate polymer and a plasticizer, and an enteric polymer component which is insoluble in aqueous systems at the pH of the stomach and soluble in aqueous systems at the higher pH of the gastrointestinal tract. The water permeable, water insoluble barrier coating comprises a blend of polymers comprising a polyvinyl acetate polymer and polyvinylpyrrolidone. The plasticizer facilitates uniform coating of the drug-ion exchange resin complex and enhances the tensile strength of the barrier coating component and thus, the hybrid coating.

The aqueous based dispersions that are used to provide a diffusion barrier coating component of the hybrid coating are characterized by having a relatively low tackiness in either the absence or presence of plasticizer(s) and provide a high percent elongation of the polymer film (elasticity) at break in the presence or absence of plasticizer(s). More specifically, the polymer film coating is characterized by exhibiting a tackiness as measured by the Hössel method described by P. Hössel, Cosmetics and Toiletries, 111 (8) 73 (1996) at 20° C./80% RH and 30° C./75% RH of about 2 or less in the presence or absence of a plasticizer and preferably about 0.5 or less.

The relatively low tack barrier coating component of the present invention provided by a polyvinyl acetate (PVA) polymer facilitates more rapid and easier processing of the coating composition and permits use of lower quantities of plasticizer. This provides for enhanced elongation (elasticity) and flexibility of the coating, a desirable property of the polymer without significantly increasing tackiness to undesirable levels due to use of a plasticizer.

Thus, the selection criteria for the plasticizer incorporated into the aqueous based polymer dispersion composition is to enhance high flexibility or elongation (elasticity) of the coating at break measured by the texture analyzer TA-XT2 HiR (Stable Microsystems) and by the method reported by the manufacturer in its literature [i.e., Jan-Peter Mittwollen, Evaluation of the Mechanical Behavior of Different Sustained Release Polymers, Business Briefing: Pharmagenerics, 2003, pp. 1-3, BASF], of at least about 100%, of at least about 125% and preferably in a range between about 150% to about 400% while not substantially increasing the tackiness of the polymer film greater than about 2 (wherein the film is measured by the Hössel method referenced above independent of any composition on which it has been deposited). The higher elasticity ranges are usually achieved with coatings of the present invention through the use of a relatively small amount of plasticizer. By using relatively small amount of plasticizer, the plasticizer does not achieve high enough levels to negatively effect the properties of the coating. It has been found that these objectives are achieved by using a relatively lower percent by weight of the selected plasticizer(s) based on the percent by weight of the solids in the aqueous based film forming polymer composition.

Generally, a plasticizer is used in the percent range, or a mixture of plasticizers combine to total, about 2 to about 30% by weight (solids content) of the coating layer, more preferably about 2.5% to about 20% by weight of the coating layer on the coated drug-ion exchange resin complex. Preferably a plasticizer in range of about 3% to about 10% by weight of the coating layer based on the coated complex provides desirable properties. However, depending upon tabletting conditions, amounts of plasticizers in the higher end of the general range provided may be desired (e.g., for high pressure compression).

Suitable plasticizers are either water soluble or water insoluble. Examples of suitable plasticizers include, e.g., dibutyl sebacate, propylene glycol, polyethylene glycol, polyvinyl alcohol, triethyl citrate, acetyl triethyl citrate, acetyl tributyl citrate, tributyl citrate, triacetin [a triester of glycerol and acetic acid, also known by the chemical name 1,3-diacetyloxypropene-2-yl acetate], and Soluphor® P [2-pyrrolidone, BASF Corp], and mixtures thereof. Other plasticizers are described in patent application publication US 2003/0099711 A1, May 29, 2003, page 4 (0041) the disclosure of which is incorporated herein by reference.

The barrier coating component is an aqueous bases polyvinyl acetate (PVA) polymer based aqueous coating dispersion which is mixed with a plasticizer as described herein. The PVA is insoluble in water at room temperature. The PVA may be used in either substantially pure form or as a blend. A commercial blend contains primarily a polyvinyl acetate polymer, a stabilizer, and minor amounts of a surfactant such as sodium lauryl sulfate. More specifically, the preferred aqueous based coating solution is KOLLICOAT SR 30 D (BASF Corporation) and whose composition is about 27% PVA polymer, about 2.7% polyvinylpyrrolidone (PVP), about 0.3% sodium lauryl sulfate (solids content 30% w/w). See, also, U.S. Pat. No. 6,066,334, which is incorporated by reference herein. The PVP and surfactant help stabilize the aqueous dispersion of the PVA. Generally, such stabilizing components are present in an amount totaling less than about 10% w/w, and preferably less than about 5% w/w. In one embodiment, if a substantially pure form of PVA is used, it can be dissolved in a suitable non-aqueous solvent with the enteric polymer component to form the hybrid coating solution for the drug ion-exchange resin complex.

Where the hybrid coating comprises a PVA polymer in the barrier coating component, the PVA polymer is present in an amount of about 70% to about 90% w/w of the barrier coating component, at least about 75%, at least about 80%, about 85% w/w of the barrier coating component.

Where the barrier coating component also comprises PVP as a stabilizer component (e.g., as is present in KOLLICOAT™ SR 30D), the barrier coating component generally contains about 5 to about 10% w/w of polyvinyl pyrrolidone.

As described above, the enteric coating selected for use in the present invention is a polymer which is insoluble at acidic pH in an aqueous system, e.g., in gastric juices, but soluble at higher pH such as are found in the lower gastrointestinal tract and is non-reactive with the barrier coating. In one embodiment, where the barrier coating comprises polyvinylacetate, the enteric coating comprises a polyvinylacetate phthalate system.

According to the present invention, the components of the hybrid coating, including, the barrier coating polymer component and the enteric coating component are mixed in order to form a homogenous mixture of the heterogeneous components. In one embodiment, the barrier coating component and the enteric coating component are dispersed in an aqueous based system, mixing at room temperature for a sufficient period of time to ensure uniform distribution of the component. Where a non-aqueous based system is used, a suitable solvent for both the barrier coating component and the enteric coating component is selected. One suitable solvent system may include, e.g., methylene chloride.

In one embodiment, the hybrid coating contains about 20:1 to about 3:1, based on solids content, of barrier coating component to enteric coating component. In a further embodiment, the hybrid coating contains 10:1 to 4:1, or about 6:1 to 4:1 barrier coating to enteric coating, based on solids content.

Suitably, the hybrid coating is applied as an aqueous dispersion using coating techniques such as are described herein, e.g., the WURSTER process. Alternatively, other coating techniques which result in uniform coating could be readily selected by one of skill in the art.

In one embodiment, the hybrid barrier coating-enteric coating is about 10% to about 60%, by weight, of the uncoated drug-ion exchange resin complex. In another embodiment, the hybrid barrier coating-enteric coating is about 25% to about 50% by weight of the uncoated drug-ion exchange resin complex, about 30% to about 45% by weight of the uncoated complex, or about 35 to about 40% by weight of the uncoated drug-ion exchange resin complex.

In one embodiment, the hybrid coating is cured and comprises a polyvinyl acetate polymeric barrier coating system commercially available as KOLLICOAT SR-30D, a plasticizer, and the enteric coating component comprising polyvinyl acetate phthalate. The coating can be cured for about 1 to about 24 hours. Alternatively, the coating is cured for about 4 to about 16 hours, and in one embodiment, at about 5 hours at high temperature, e.g., about 50° C. to about 65° C., and preferably about 60° C.

The resulting coated particles are within the size range described herein, i.e., they are preferably below about 420 microns in size, with the majority falling within the range of about 40 micron to about 250 micron range.

Optionally, a non-functional film coating may be applied on the exterior of the tablet, e.g., to permit application of a gloss coat or a dye. Such a non-functional coating does not affect the release profile of the dosage unit. Such a coating may be present in an amount of about 1 to 10% w/w of the coated particle, and more preferably, about 1 to about 5% w/w of the coated particle. Examples of suitable coating compositions include those which are commercially available, e.g., the OPADRY series from Colorcon. See, U.S. Pat. No. 4,543,370, the disclosure of which is incorporated by reference.

Suitably, the coated drug-ion exchange resin complexes of the invention are still within the size range identified above. The coated drug-ion exchange resin composition may be stored for future use, packaged, or promptly formulated with conventional pharmaceutically acceptable carriers to prepare finished ingestible compositions for delivery orally, nasogastric tube, or via other means. The compositions according to this invention may, for example, take the form of solid preparations such as capsules (which may include liquigels or the granular hybrid coated ion exchange resin complexes), powders, tablets, caplets, etc.

Finished Formulations

The hybrid coated drug-ion exchange resin complexes of the present invention, can readily be formulated with pharmaceutically acceptable excipients according to methods well known to those of skill in the art. In one embodiment, these formulations contain a coated opioid drug-ion exchange resin complex of the invention, optionally with a release retardant. In another embodiment, such formulations may also contain a selected amount of uncoated drug-ion exchange resin complex, optionally with a release retardant as described herein.

In yet another embodiment, the formulations of the invention may contain more than one active component. For example, the formulation may contain more than one drug loaded into an ion exchange resin to form a complex of the invention.

The coated drug-ion exchange resin complex of the invention may be formulated for delivery by any suitable route. However, the complex is particularly well suited for oral delivery and is so formulated.

In one particularly desirable embodiment, the coated drug-ion exchange resin complex of the invention is formulated into a solid oral dose form such as a modified release tablet or granules in a capsule. In one embodiment, the solid dosage form contains at least one hybrid coated opioid-ion exchange resin complex of the invention in admixture with components such as fillers, lubricants, and disintegrants. In one embodiment, one or more fillers is present in an amount of about 1 to 70% w/w of the dosage unit. For example, a dosage unit may contain about 5 to 15% w/w calcium silicate, about 10 to 50% w/w microcrystalline cellulose, about 10 to about 50% w/w lactose, or combinations of these fillers/diluents. In another embodiment, one or more lubricants may be present in an amount of about 0.01% to about 5% w/w of the dosage unit. For example, a dosage unit may contain about 0.2 to about 2% w/w amorphous silica, about 0.5 to about 5% w/w talc, about 0.05 to about 1.5% magnesium stearate, or combinations of these lubricants. In one embodiment, the solid dosage unit contains about 1 to about 20% w/w of a disintegrant. For example, about 4 to about 8% w/w crospovidone may be present in the solid dosage unit alone or in combination with another disintegrant.

The drug-ion exchange resin coated compositions may be formulated using conventional pharmaceutically acceptable carriers or excipients and well established techniques. Without being limited thereto, such conventional carriers or excipients include diluents (e.g., microcrystalline cellulose, lactose), fillers (e.g., calcium silicate), binders and adhesives (i.e., cellulose derivatives and acrylic derivatives), lubricants (i.e., magnesium or calcium stearate, or vegetable oils, polyethylene glycols, talc, sodium lauryl sulfate, amorphous silica, polyoxy ethylene monostearate), thickeners, solubilizers, humectants, disintegrants (e.g., crospovidone), colorants, flavorings, stabilizing agents, sweeteners, and miscellaneous materials such as buffers and adsorbents in order to prepare a particular pharmaceutical composition. The stabilizing agents may include preservatives and anti-oxidants, amongst other components which will be readily apparent to one of ordinary skill in the art.

When formulated into a liquid suspension, a variety of these or additional excipients may be included. For example, a suspension may contain thickeners or humectants. Suitable thickeners include, e.g., tragacanth; xanthan gum; bentonite; starch; acacia and lower alkyl ethers of cellulose (including the hydroxy and carboxy derivatives of the cellulose ethers). Examples of cellulose include, e.g., hydroxypropyl cellulose, hydroxypropyl methyl cellulose, sodium carboxy methylcellulose, microcrystalline cellulose (MCC), and MCC with sodium carboxylmethyl cellulose. In one embodiment, tragacanth is used and incorporated in an amount of from about 0.1 to about 1.0% weight per volume (w/v) of the composition, and more preferably about 0.5% w/v of the composition. Xanthan gum is used in the amount of from about 0.025 to about 0.5% w/v and preferably about 0.25% w/v. A humectant may be included to give the suspension greater viscosity and stability. Suitable humectants useful in the finished formulations include glycerin, polyethylene glycol, propylene glycol and mixtures thereof.

Oral liquid suspensions of the present invention may also comprise one or more surfactants in amounts of up to about 5.0% w/v and preferably from about 0.02 to about 3.0% w/v of the total formulation. The surfactants useful in the preparation of the finished compositions of the present invention are generally organic materials which aid in the stabilization and dispersion of the ingredients in aqueous systems for a suitable homogenous composition. Preferably, the surfactants of choice are non-ionic surfactants such as poly(oxyethylene)(20) sorbitan monooleate and sorbitan monooleate. These are commercially known as TWEENS and SPANS and are produced in a wide variety of structures and molecular weights.

Whereas any one of a number of surfactants may be used, preferably a compound from the group comprising polysorbate copolymers (sorbitan-mono-9-octadecenoate-poly(oxy-1,2-ethanediyl)) is employed. This compound is also added functions to keep any flavors and sweeteners homogeneously dissolved and dispersed in solution.

Suitable polysorbates include polysorbate 20, polysorbate 40, polysorbate 80 and mixtures thereof. Most preferably, polysorbate 80 is employed. The surfactant component will comprise from about 0.01 to about 2.0% w/v of the total composition and preferably will comprise about 0.1% w/v of the total weight of the composition.

A second emulsifer/surfactant useful in combination with polysorbates may be employed and is preferably a poloxamer such as Poloxamer 407. Poloxamer 407 has an HLB (hydrophilic/lipophilic balance) of about 22 and is sold under the tradename Plutonic-127 (BASF-NJ). The two surfactants can be employed in substantially equivalent amounts. For example, the Poloxamer 407 and polysorbate 80 may each be employed together at levels of approximately from about 0.02 to about 4.0% w/v of the total weight of the formulation.

Aqueous suspensions may be obtained by dispersing the drug-ion exchange resin compositions in a suitable aqueous vehicle, optionally with the addition of suitable viscosity enhancing agent(s) (e.g., cellulose derivatives, xanthan gum, etc). Non-aqueous suspensions may be obtained by dispersing the foregoing compositions in a suitable non-aqueous based vehicle, optionally with the addition of suitable viscosity enhancing agent(s) (e.g., hydrogenated edible fats, aluminum state, etc.). Suitable non-aqueous vehicles include, for example, almond oil, arachis oil, soybean oil or soybean oil or fractionated vegetable oils such as fractionated coconut oil.

Useful preservatives include, but are not limited to, sodium benzoate, benzoic acid, potassium sorbate, salts of edetate (also known as salts of ethylenediaminetetraacetic acid, or EDTA, such as disodium EDTA), parabens (e.g., methyl, ethyl, propyl or butyl-hydroxybenzoates, etc.), and sorbic acid. Amongst useful preservatives include chelating agents some of which are listed above and other chelating agents, e.g., nitrilotriacetic acid (NTA); ethylenediaminetetraacetic acid (EDTA), hydroxyethylethylenediaminetriacetic acid (HEDTA), diethylenetriaminepentaacetic acid (DPTA), 1,2-Diaminopropanetetraacetic acid (1,2-PDTA); 1,3-Diaminopropanetetraacetic acid (1,3-PDTA); 2,2-ethylenedioxybis [ethyliminodi(acetic acid)] (EGTA); 1,10-bis(2-pyridylmethyl)-1,4,7,10-tetraazadecane (BPTETA); ethylenediamine (EDAMINE); Trans-1,2-diaminocyclohexane-N,N,N',N'-tetraacetic acid (CDTA); ethylenediamine-N,N'-diacetate (EDDA); phenazine methosulphate (PMS); 2,6-Dichloro-indophenol (DCPIP); Bis(carboxymethyl)diaza-18-crown-6 (CROWN); porphine; chlorophyll; dimercaprol (2,3-Dimercapto-1-propanol); citric acid; tartaric acid; fumaric acid; malic acid; and salts thereof. The preservatives listed above are exemplary, but each preservative must be evaluated in each formulation, to assure the compatibility and efficacy of the preservative. Methods for evaluating the efficacy of preservatives in pharmaceutical formulations are known to those skilled in the art. Preferred preservatives are the paraben preservatives including, methyl, ethyl, propyl, and butyl paraben. Methyl and propyl paraben are most preferable. Preferably, both methyl and propyl paraben are present in the formulation in a ratio of methyl paraben to propyl paraben of from about 2.5:1 to about 16:1, preferably 9:1.

In the instance where auxiliary sweeteners are utilized, the present invention contemplates the inclusion of those sweeteners well known in the art, including both natural and artificial sweeteners. Thus, additional sweeteners may be chosen from the following non-limiting list: Water-soluble sweetening agents such as monosaccharides, disaccharides and polysaccharides such as xylose, ribose, glucose, mannose, galactose, fructose, high fructose corn syrup, dextrose, sucrose, sugar, maltose, partially hydrolyzed starch, or corn syrup solids and sugar alcohols such as sorbitol, xylitol, mannitol and mixtures thereof.

In general, the amount of sweetener will vary with the desired amount of sweeteners selected for a particular liquid suspension. This amount will normally be 0.001 to about 90% by weight, per volume of the final liquid suspension composition, when using an easily extractable sweetener. The water-soluble sweeteners described above, are preferably used in amounts of about 5 to about 70% by weight per volume, and most preferably from about 10 to about 50% by weight per volume of the final liquid suspension composition. In contrast, the artificial sweeteners [e.g., sucralose, acesulfame K, and dipeptide based sweeteners] are used in amounts of about 0.005 to about 5.0% and most preferably about 0.01 to about 2.5% by weight per volume of the final liquid suspension composition. These amounts are ordinarily necessary to achieve a desired level of sweetness independent from the flavor level achieved from flavor oils.

Suitable flavorings include both natural and artificial flavors, and mints such as peppermint, menthol, artificial vanilla, cinnamon, various fruit flavors, both individual and mixed, essential oils (i.e., thymol, eucalyptol, menthol and methyl salicylate) and the like are contemplated. The amount of flavoring employed is normally a matter of preference subject to such factors as flavor type, individual flavor, and strength desired. Thus, the amount may be varied in order to obtain the result desired in the final product. Such variations are within the capabilities of those skilled in the art without the need for undue experimentation. The flavorings are generally utilized in amounts that will vary depending upon the individual flavor, and may, for example, range in amounts of about 0.01 to about 3% by weight per volume of the final composition weight.

The colorants useful in the present invention include the pigments such as titanium dioxide that may be incorporated in amounts of up to about 1% by weight per volume, and preferably up to about 0.6% by weight per volume. Also, the colorants may include dyes suitable for food, drug and cosmetic applications, and known as D&C and F.D. & C. dyes and the like. The materials acceptable for the foregoing spectrum of use are preferably water-soluble. Illustrative examples include indigo dye, known as F.D. & C. Blue No. 2, which is the disodium salt of 5,5-indigotindisulfonic acid. Similarly, the dye known as F.D. & C. Green No. 1 comprises a triphenylmethane dye and is the monosodium salt of 4-[4-N-ethyl p-sulfobenzylamino)diphenylmethylene]-[1-(N-ethyl-N-p-sulfoniumbenzyl)-2,5-cyclohexadienimine]. A full recitation of all F.D. & C. and D. & C. and their corresponding chemical structures may be found in the Kirk-Othmer Encyclopedia of Chemical Technology, in Volume 5, at Pages 857-884, which text is accordingly incorporated herein by reference. Optionally, these or similar components may also be included in a non-functional coating for a tablet.

Suitable oils and fats that are usable would include partially hydrogenated vegetable or animal fats, such as coconut oil, palm kernel oil, beef tallow, lard, and the like. These ingredients are generally utilized in amounts with respect to the ingestible product of up to about 7.0% by weight, and preferably up to about 3.5% by weight of the final product.

Wetting agents also may be employed in the inventive compositions to facilitate the dispersion of any hydrophobic ingredients. The concentration of wetting agents in the composition should be selected to achieve optimum dispersion of the ingredient within the composition with the lowest feasible concentration of wetting agent. It should be appreciated that an excess concentration of wetting agent may cause the composition, as a suspension, to flocculate. Those skilled in the art are well versed in suitable empirical methods to determine the appropriate wetting agents and concentrations to achieve optimum dispersion and avoid flocculation. Suitable wetting agents are listed in the US Pharmacoepia 29.

Where desired, the hybrid coated drug-ion exchange granules or particles of the invention are loaded into a capsule. Typically, a capsule is a shell which readily dissolves in the stomach and can be made from a variety of orally ingestible products (e.g., gelatin, hydroxypropylmethylcellulose (vegetarian)). Thus, the capsule does not affect the release profile of the composition of the invention. Suitable capsule shells are readily obtained from a variety of commercial sources including, e.g., Capsuline, CapsuleGel, Shinogi, and United Capsules). Typically, the capsule shell selected is of size 0 or 1. The amount of granules loaded into the capsule depends upon the size of the capsule and the amount of active desired. For example, where the drug is designed to provide the equivalent of 100 mg of morphine sulfate, 450 mg of hybrid coated morphine-cation exchange resin may be loaded into a size 0 capsule. However, other suitable shell sizes can be readily determined.

Optionally, where needed to facilitate flow while filling a capsule, a coated drug-ion exchange resin complex may be mixed with a lubricant. Suitable lubricants can be readily selected from among those known in the art, e.g., magnesium stearate, talc, etc.

The following examples are provided to more specifically illustrate the modified release compositions of the present invention and not intended to be limiting. They are for illustrative purposes only and it is realized that changes and variations can be made without departing from the spirit and scope of the invention.

Example 1

Preparation of Hybrid Coated Morphine Resin Complex

The following example describes the preparation of a hybrid coated morphine-ion exchange resin complex, in which the cation exchange resin utilized is the Amberlite IRP-69 brand cross-linked polysytrene resin. The formed morphine—ion exchange resin complex may be referred to as morphine polistyrex for convenience.

| Ingredient | Quantity |
|---|---|
| Morphine Resin Complex | |
| Morphine Sulfate | 810 g |
| Purified Water | 13600 g |
| AMBERLITE IRP-69 RESIN | 1358 g |
| KOLLIDON K-30 polyvinylpyrrolidone | 180 g |
| Purified water | 421 g |
| Coated Morphine Resin Complex | |
| KOLLICOAT SR-30D polymer system | 693.38 g |
| (30% dispersion) | (208.0164 g solids) |
| Triacetin | 10.37 g |
| SURETERIC 90G18507 White polyvinylacetate phthalate polymer system | 41.6 g |
| Purified Water | 554.65 g |
| Morphine Resin Complex | 600 g |

The following was performed at room temperature unless otherwise specified. The morphine resin complex was prepared by first dissolving 810 g of morphine sulfate in 13.6 liters of purified water, and then slowly adding 1358 g of AMBERLITE™ IRP-69 resin with continuous mixing using a propeller mixer (ARROW™). The dispersion was mixed for 1 hour and upon completion, the dispersion was filtered through a Buchner funnel with the aid of vacuum. The dispersion/filtration process was repeated twice with 4800 g of purified water. The wet resin complex was then dried in a VECTOR™ FLM-1 fluid bed processor at 50° C. until the moisture content was about 15-25%. In a separate container 180 g of KOLLIDON K-30™ polyvinylpyrrolidone (PVP) was added into 421 g of purified water and mixed using a propeller mixer (ARROW™) until dissolved. The aqueous KOLLIDON K-30™ PVP solution was then slowly added to the wet resin complex in a Hobart type mixer (KitchenAid) to form a uniform mass. The wet mass was again dried at 50° C. in a VECTOR™ FLM-1 fluid bed processor to a moisture content of about 15-25%, thereby forming granules. The semi-dried granules were then milled through a 40 mesh screen using CO-MIL™ brand mill and drying continued under 50° C. until the moisture content was between 3-7%. The dried granules were then milled through a 40 mesh screen using CO-MIL™ brand mill [QUADRO]. The 40 mesh screen allows particles of less than 420 microns to pass through.

In a separate container, 10.37 g of triacetin and 693.38 g of KOLLICOAT™ SR-30D (which is a 30% dispersion of a polyinyl acetate polymer system as described above) were mixed for 1 hour (solution-A). 41.6 g of SURETERIC™ 90G 18507 White polyinylacetate phthalate (PVAP) was dispersed in 554.65 g of purified water and mixed for 30 minutes (solution-B) using a propeller mixer (ARROW™). Solution-B was added into Solution-A and mixed for 1 hour using a propeller mixer (ARROW™). The final coating solution was passed through a 40 mesh screen. The coating process was performed in a VECTOR™ FLM-1 fluid bed processor by applying 1,200 g of coating solution to 600 g of Morphine Resin Complex using the WURSTER process that resulted in 40% weight gain. The coating conditions were controlled at a product temperature of 25-35° C., air flow of 10-25 cfm, nozzle pressure of 2-3 kg/cm², accelerator air pressure of 1 kg/cm², and spray rate of 2.5-10 g/min so that uniform coating was achieved. The coated Morphine Resin Complex was then placed at 60° C. in a VWR™ convection oven for 5 hours.

The resulting hybrid coated morphine resin complex still passes through a 40 mesh screen.

The dried hybrid coated morphine resin complex is ready for tabletting (Example 2), formulation into a suspension (Example 3) or assembly into a capsule (Example 4).

| Ingredient | Quantity |
|---|---|
| Hybrid coated Morphine Ion Resin Complex (from example 1) | 266.84 g |
| Calcium silicate, (RXCIPIENT ™ FM1000) | 40.5 g |
| Silicon dioxide, (RXCIPIENT ™ GL100) | 4.5 g |
| Microcrystalline cellulose, (AVICEL ® PH 101) | 127.74 g |
| Crospovidone, (KOLLIDON ™ CL-SF) | 18 g |
| Lactose monohydrate, (FLOWLAC ™ 100) | 96.6 g |
| Talc (IMPERIAL ™ 500) | 9 g |
| Magnesium Stearate | 2.1 g |
| TOTAL | 565.28 g |
| Hybrid Coated Morphine Modified Release tablets | |
| OPADRY ® WHITE YS-1-18202-A-PVAP | 20 g |
| Purified water | 80 g |
| Hybrid Coated Morphine ER tablets | 200 g |

Hybrid coated Morphine Ion Resin Complex (266.84 g, from example 1), calcium silicate (RXCIPIENT™ FM1000) (40.5 g), silicon dioxide (RXCIPIENT™ GL100) (4.5 g), microcrystalline cellulose (AVICEL® PH 101) (127.74 g), crospovidone (KOLLIDON™ CL-SF) (18 g), lactose monohydrate (FLOWLAC™ 100) (96.6 g), and talc (IMPERIAL™ 500) (9 g) were passed through 40 mesh screen and mixed for 10 minutes using a cube blender (ERWEKA™ AR-402). Magnesium stearate (2.1 g) was passed through 40 mesh screen and added into the blender and further mixed for 5 minutes. The blend was compressed into tablets using a rotary tablet press (MINI PRESS™) fitted with a 0.3440"×0.7500" capsule shape tooling. Tablets were compressed with weight of 942.14 mg (equivalent to 100 mg morphine sulfate), hardness of 7-11 kp, at machine speed of 5-30 rpm, resulting in tablets of approximately 1 gram each in size.

In order to provide a desired, non-functional coating on the tablets, OPADRY®WHITE YS-1-18202-A (20 g) was dispersed into 80 g purified water and mixed for 45 minutes using a propeller mixer (ARROW™). The coating process was performed in a perforated coating pan (VECTOR™ LDCS-5) by applying 20 g of coating solution to 200 of the approximately 1 g Morphine-Ion Exchange Modified Release tablets to provide about a 2% wt gain to each tablet.

The coating conditions were controlled using an exhaust temperature of 30° C. and a spray rate of 5 g/min.

This tableted form of the hybrid coated morphine-cation exchange resin complex exemplified in Example 2 was designed to have desired abuse resistance and an in vivo release profile essentially the same as the currently commercially available Kadian® 100 mg morphine sulfate capsule which has a 12-24 hours extended release formulation.

In vitro dissolution was assessed in the USP Standard paddle test (apparatus 2), at a speed of 50 rpm, a bath temperature of 37±0.5° C., in a dissolution medium of 500 mL 0.1 N hydrochloric acid for 1 hour, followed by addition of 500 mL of phosphate buffer to a pH 7.5. The tableted form of the hybrid coated morphine-cation exchange resin complex has an in vitro dissolution release rate of morphine of 11.4% in 1 hour, 49.4% in 2 hours, 67.4% in 3 hours, 77.0% in 4 hours, and 95.1% in 12 hours. It will be understood by one of skill in the art that two compositions can have different in vitro dissolution rates, yet provide bioequivalent in vivo release rates.

| Ingredient | Quantity |
|---|---|
| Placebo Suspension Base | |
| Citric acid, anhydrous | 8 g |
| High Fructose Corn Syrup 42 | 1,200 g |
| Sucrose | 600 g |
| Starch | 92 g |
| Xanthan gum | 7.6 g |
| Glycerin | 400 g |
| Methylparaben | 7.2 g |
| Propylparaben | 0.8 g |
| Strawberry Banana Flavor | 44.88 g |
| Purified Water | QS 3484.91 g |
| Hybrid Coated Morphine-Ion Exchange Resin Complex Modified Release Suspension | |
| Purified Water | 200 g |
| Sodium Metabisulfite | 1 g |
| Polysorbate 80 | 1 g |
| Hybrid Coated Morphine Ion Exchange Resin (From Example 1) | 18.59 g |
| Placebo Suspension Base | 871.2 g |
| Purified Water | QS 1,000 mL |

A placebo suspension base was prepared by first dissolving 8 g of citric acid in an appropriate amount of purified water, followed by adding 600 g of sucrose and 1200 g of high fructose corn syrup to achieve complete solution. 92 g of starch was then slowly introduced to the main container under high shear mixing condition to achieve uniform dispersion. In another container, 400 g glycerin was added and heated to 45-50° C. followed by addition of 7.2 g of methylparaben and 0.8 g propylparaben. After both of the parabens were completely dissolved, the solution was cooled to room temperature and 7.6 g Xanthan gum was slowly introduced to the solution to form a uniform dispersion. The gum dispersion was then transferred to the main container under high speed/ shear mixing condition to achieve uniform suspension. 44.88 g of Strawberry/Banana flavor was added and the Placebo suspension base was achieved by addition of the remaining purified water and mixed until uniform.

To prepare the suspension, 200 g water was weighed to the main container followed by the addition of 1 g of Sodium Metabisulfite and Polysorbate 80. These components were mixed until completely dissolved. 871.2 g of Placebo Suspension Base was then added. The hybrid coated morphine ion exchange complex of example 1 was then added slowly under conditions of gentle mixing. The final suspension was obtained by adding an appropriate amount of purified water to make up the volume to 1000 mL followed by gentle mixing until a uniform suspension is obtained.

| Ingredient | Quantity |
|---|---|
| Coated Morphine Ion Exchange Resin Complex (From Example 1) | 450 g |
| Magnesium Stearate | 4.5 g |

A hybrid coated morphine-ion exchange resin complex that may be prepared according to example 1 is taken and blended with 1% Magnesium Stearate in a cube blender for 3 minutes at batch scale.

Approximately 454 mg of the blend is then filled into a Size 0 hard gelatin capsule to provide an amount of active equivalent to 100 mg morphine sulfate.

Example 5

Preparation of Hybrid Coated Morphine-Resin Complex

This example illustrates the preparation of a hybrid coated opioid-ion exchange resin complex with a different hybrid coating than that illustrated in Example 1. This hybrid coating contains a higher percentage of the barrier coating polymer as compared to the enteric polymer.

| Ingredient | Quantity |
|---|---|
| Morphine Resin Complex | |
| Morphine Sulfate | 810 g |
| Purified Water | 13600 g |
| AMBERLITE IRP-69 RESIN | 1358 g |
| KOLLIDON K-30 ™ (PVP) | 180 g |
| Purified water | 421 g |
| Hybrid coated Morphine Resin Complex | |
| KOLLICOAT SR-30D ™ polymer system (30% dispersion) | 770.42 g (231.126 g solids) |
| Triacetin | 11.53 g |
| SURETERIC ™ 90G18507 White brand (PVAP) | 17.34 g |
| Purified Water | 500.71 g |
| Morphine Resin Complex | 600 g |

The morphine ion exchange resin complex was prepared by first dissolving 810 g of morphine sulfate in 13.6 liters of purified water, and then slowly adding 1358 g of AMBERLITE™ IRP-69 resin with continuous mixing using a propeller mixer (ARROW™). The dispersion was mixed for 1 hour and upon completion, the dispersion was filtered through a Buchner funnel with the aid of vacuum. The dispersion/filtration process was repeated twice with 4800 g of purified water. The wet resin complex was then dried in a VECTOR™ FLM-1 fluid bed processor at 50° C. until moisture content was about 15-25%. In separate container 180 g of KOLLIDON™ K-30 PVP was added into 421 g of purified water and mixed using propeller mixer (ARROW™) until dissolved. The aqueous KOLLIDON™ K-30 solution was then slowly added to the wet resin complex in a Hobart type mixer (Kitchen Aid) to form a uniform mass. The wet mass was again dried at 50° C. in a VECTOR™ FLM-1 fluid bed processor to the moisture content about 15-25%. The semi-dried granules were then milled through a 40 mesh screen using CO-MIL™ brand mill and continued drying under 50° C. until the moisture content was between 3-7%. The dried granules were then milled through a 40 mesh screen using CO-MIL™ brand mill [QUADRO].

In separate container, 11.53 g of triacetin and 770.42 g of KOLLICOAT™ SR-30D polymer system were mixed for 1 hour (solution-A). 17.34 g of SURETERIC™ 90G18507 white PVAP was dispersed in 500.71 g of purified water and mixed for 30 minutes (solution-B) using propeller mixer (ARROW™). Solution-B was added into Solution-A and mixed for 1 hour using propeller mixer (ARROW™). The final coating solution was passed through 40 mesh screen. The coating process was performed in a VECTOR™ FLM-1 fluid bed processor by applying 1,200 g of hybrid coating solution to 600 g of Morphine Ion Resin Complex of this example using the WURSTER process that resulted in 40% weight gain. The coating conditions were controlled at a product temperature of 25-35° C., air flow of 10-25 cfm, nozzle pressure of 2-3 kg/cm2, accelerator air pressure of 1 kg/cm2, and spray rate of 2.5-10 g/min so that uniform coating was achieved. The coated Morphine Resin Complex was then placed at 60° C. in a VWR™ convection oven for 5 hours.

Example 6

Preparation of Hybrid Coated Morphine Resin Complex

This example illustrates the preparation of a coated opioid-ion exchange resin complex with a different hybrid coating than that illustrated in Example 1 (or Example 5). This hybrid coating contains a higher percentage by weight of the enteric coating polymer as compared to the percentage of this component in Example 1 (and Example 5).

| Ingredient | Quantity |
| --- | --- |
| Morphine Ion Exchange Resin Complex | |
| Morphine Sulfate | 810 g |
| Purified Water | 13600 g |
| AMBERLITE IRP-69 Resin | 1358 g |
| KOLLIDON K-30 PVP | 180 g |
| Purified water | 421 g |
| Coated Morphine Ion Resin Complex | |
| KOLLICOAT SR-30D polymer system (30% dispersion) | 641.979 g (192.5937 g solids) |
| Triacetin | 9.633 g |
| SURETERIC 90G18507 White PVAP system | 57.785 g |
| Purified Water | 590.603 g |
| Morphine Resin Complex | 600 g |

The morphine resin complex was prepared by first dissolving 810 g of morphine sulfate in 13.6 liters of purified water, and then slowly adding 1358 g of AMBERLITE™ IRP-69 resin with continuous mixing using propeller mixer (ARROW™). The dispersion was mixed for 1 hour and upon completion, the dispersion was filtered through a filtration apparatus (Buchner funnel) with the aid of vacuum. The dispersion/filtration process was repeated twice with 4800 g of purified water. The wet resin complex was then dried in a VECTOR™ FLM-1 fluid bed processor at 50° C. until moisture content was about 15-25%. In separate container 180 g of KOLLIDON™ K-30 PVP was added into 421 g of purified water and mixed using propeller mixer (ARROW™) until dissolved. The KOLLIDON™ K-30 PVP solution was then slowly added to the wet resin complex in a Hobart type mixer (Kitchen Aid) to form uniform mass. The wet mass was again dried at 50° C. in a VECTOR™ FLM-1 fluid bed processor to the moisture content around 15-25%. The semi-dried granules were then milled through a 40 mesh screen using CO-MIL™ brand mill and continued drying under 50° C. until the moisture content was between 3-7%. The dried granules were then milled through a 40 mesh screen using CO-MIL™ brand mill [QUADRO].

In a separate container, 9.633 g of triacetin and 641.979 g of KOLLICOAT™ SR-30D polyvinylacetate polymer system were mixed for 1 hour (solution-A). 57.785 g of SURETERIC™ 90G18507 white PVAP was dispersed in 590.603 g of purified water and mixed for 30 minutes (solution-B) using a propeller stirrer (ARROW™). Solution-B was added into Solution-A and mixed for 1 hour using a propeller stirrer (ARROW™). The final coating solution was passed through 40 mesh screen. The coating process was performed in a VECTOR™ FLM-1 fluid bed processor by applying 1,200 g of coating solution to 600 g of Morphine Resin Complex using WURSTER process that resulted in 40% weight gain. The coating conditions were controlled at an product temperature of 25-35° C., air flow of 10-25 cfm, nozzle pressure of 2-3 kg/cm$^2$, accelerator air pressure of 1 kg/cm$^2$, and spray rate of 2.5-10 g/min so that uniform coating was achieved. The coated Morphine Resin Complex was then placed at 60° C. in VWR™ convection oven for 5 hours.

| Ingredient | Quantity |
| --- | --- |
| Morphine Resin Complex | |
| Morphine Sulfate | 450 g |
| Purified Water | 5 L |
| AMBERLITE IRP-69 Resin | 807 g |
| KOLLICOAT SR-30D polymer system | 501 g |
| Coated Morphine Resin Complex | |
| KOLLICOAT SR-30D polymer system (30% dispersion) | 693.38 g |
| Triacetin | 10.37 g |
| SURETERIC 90G 18507 White PVAP system | 41.6 g |
| Purified Water | 554.65 g |
| Morphine Resin Complex | 600 g |

The morphine resin complex is prepared by first dissolving 450 g of morphine sulfate in 5 liters of purified water, and then slowly adding 807 g of AMBERLITE™ IRP-69 resin with continuous mixing. The dispersion is mixed for 1 hour and upon completion, the dispersion is filtered through a filtration apparatus such as a Buchner funnel with the aid of vacuum. The dispersion/filtration process is repeated twice with 4800 g of purified water. The wet resin complex is then dried in a VECTOR™ FLM-1 fluid bed processor at 50° C. until moisture content is about 15-25%. KOLLICOAT™ SR-30D of 501 g is then slowly added to the wet resin complex in a Hobart type mixer (Kitchen Aid) to form a uniform mass. The wet mass is again dried at 50° C. in a VECTOR™ FLM-1 fluid bed processor to the moisture content around 20%. The semi dried granules are then milled through a 40 mesh screen using CO-MIL™ brand mill and drying continued at 50° C. until the moisture content is about 3-7%. The dried granules are then milled through a 40 mesh screen using CO-MIL™ brand mill [QUADRO].

In a separate container, 10.37 g of triacetin and 693.38 g of KOLLICOAT™ SR-30D PVA polymer system are mixed for 1 hour (solution-A). SURETERIC™ 90G 18507 White PVAP is dispersed in 554.65 g of purified water and mixed for 30 minutes (solution-B) using propeller mixer (ARROW™). Solution B is added into Solution A and mixed for 1 hour using propeller mixer (ARROW™). The final coating is passed through 40 mesh screen. The coating process is performed in a VECTOR™ FLM-1 fluid bed processor by applying 1,200 g of coating solution to 600 g of Morphine Resin Complex using the WURSTER process that resulted in 40% weight gain. The coating conditions are controlled at an inlet temperature of 25-35° C., air flow of 10-25 cfm, nozzle pressure of 2-3 kg/cm$^2$, accelerator air pressure of 1 kg/cm$^2$, and spray rate of 2.5-10 g/min so that uniform coating is achieved. The coated Morphine Resin complex is then placed at 60° C. in VWR™ convection oven for 5 hours.

The dried coated morphine resin complex is ready for formulation, e.g., as described in Example 8.

| Ingredient | Quantity |
|---|---|
| Hybrid coated Morphine Resin Complex (from example 7) | 266.84 g |
| Calcium silicate (RXCIPIENT ™ FM 1000) | 40.5 g |
| Silicon dioxide (RXCIPIENT ™ GL 100) | 4.5 g |
| Microcrystalline cellulose (AVICEL ® PH 101) | 127.74 g |
| Crospovidone (KOLLIDON ™ CL-SF) | 18 g |
| Lactose monohydrate (FLOWLAC ™ 100) | 96.6 g |
| Talc (IMPERIAL ™ 500) | 9 g |
| Magnesium Stearate | 2.1 g |
| TOTAL (uncoated tablet) | 565.28 g |
| Hybrid Coated Morphine Modified Release Tablets | |
| OPADRY ® WHITE YS-1-18202-A | 20 g |
| Purified water | 80 g |
| Morphine Modified Release Tablets (containing coated morphine resin complex) | 200 g |

Hybrid coated Morphine Resin Complex (from example 7) (266.84 g), calcium silicate (RXCIPIENT™ FM 1000) (40.5 g), silicon dioxide (RXCIPIENT™ GL 100) (4.5 g), microcrystalline cellulose (AVICEL® PH 101) (127.74 g), crospovidone (KOLLIDON™ CL-SF) (18 g), lactose monohydrate (FLOWLAC™ 100) (96.6 g), and talc (IMPERIAL™ 500) (9 g) are passed through 40 mesh screen and mixed for 10 minutes using a cube blender (ERWEKA™ AR-402). Magnesium stearate (2.1 g) is passed through 40 mesh screen and added into blender and further mixed for 5 minutes. The blend is compressed into tablets using a rotary tablet press (MINIPRESS™ fitted with a 0.3344×0.7500 capsule shape tooling. Tablets are compressed with weight of 942.14 mg (equivalent to 100 mg morphine sulfate), hardness of 7-11 kp, at machine speed of 5-30 rpm.

A non-functional coating may be prepared and applied as follows. OPADRY® WHITE YS-1-18202-A brand (20 g) is dispersed into 80 g purified water and mixed for 45 minutes using propeller mixer (ARROW™). The coating process is performed in a perforated coating pan (VECTOR™ LDCS-5) by applying 20 g of coating solution to 200-1 g Morphine ER tablets. The coating conditions are controlled by exhaust temperature of 30° C. and spray rate of 5 g/min.

| Ingredient | Quantity |
|---|---|
| Oxycodone Resin Complex | |
| Oxycodone HCl | 450 g |
| Purified Water | 5 L |
| AMBERLITE IRP-69 Resin | 1,427 g |
| KOLLICOAT SR-30D polymer system (30% dispersion) | 500 g |
| Coated Oxycodone Resin Complex | |
| KOLLICOAT SR-30D polymer system (30% dispersion) | 693.38 g |
| Triacetin | 10.37 g |
| SURETERIC 90G 18507 White PVAP system | 41.6 g |
| Purified Water | 554.65 g |
| Oxycodone Ion Exchange Resin Complex | 600 g |

An Oxycodone ion exchange resin complex may be prepared in accordance with the present invention as follows. 450 g of oxycodone HCl is dissolved in 5 liters of purified water, and then slowly adding 807 g of AMBERLITE™ IRP-69 resin with continuous mixing. The dispersion is mixed for 1 hour and upon completion, filter the dispersion through a filtration apparatus (Buchner funnel) with the aid of vacuum. The dispersion/filtration process is repeated twice with 4800 g of purified water. The wet resin complex is then dried in a VECTOR™ FLM-1 fluid bed processor at 50° C. until moisture content is about 15-25%. KOLLICOAT™ SR-30D of 501 g is then slowly added to the wet resin complex in a Hobart type mixer (Kitchen Aid) to form a uniform mass. The wet mass is again dried at 50° C. in a VECTOR™ FLM-1 fluid bed processor to the moisture content around 20%. The semi dried granules are then milled through a 40 mesh screen using CO-MIL™ brand mill and continued drying at 50° C. until moisture content is about 3-7%. The dried granules are then milled through a 40 mesh screen using CO-MIL™ brand mill [QUADRO].

In a separate container, 10.37 g of triacetin and 693.38 g of KOLLICOAT™ SR-30D are mixed for 1 hour (solution-A). SURETERIC™ 90G 18507 White is dispersed in 554.65 g of purified water and mixed for 30 minutes (solution-B) using propeller mixer (ARROW™). Solution B is added into Solution A and mixed for 1 hour using propeller mixer (ARROW™). The final coating is passed through 40 mesh screen. The coating process is performed in a VECTOR™ FLM-1 fluid bed processor by applying 1,200 g of coating solution to 600 g of Oxycodone Resin Complex using WURSTER process that results in 40% weight gain. The coating conditions are controlled at an inlet temperature of 25-35° C., air flow of 10-25 cfm, nozzle pressure of 2-3 kg/cm$^2$, accelerator air pressure of 1 kg/cm$^2$, and spray rate of 2.5-10 g/min so that uniform coating is achieved. The coated oxycodone complex is then placed at 60° C. in VWR™ convection oven for 5 hours.

| Ingredient | Quantity |
|---|---|
| Hybrid Coated Oxycodone Resin Complex (from example 9) | 266.84 g |
| Calcium silicate (RXCIPIENT ™ FM 1000) | 40.5 g |
| Silicon dioxide (RXCIPIENT ™ GL 100) | 4.5 g |
| Microcrystalline cellulose (AVICEL ® PH 101) | 127.74 g |
| Crospovidone (KOLLIDON ™ CL-SF) | 18 g |
| Lactose monohydrate (FLOWLAC ™ 100) | 96.6 g |
| Talc (IMPERIAL ™ 500) | 9 g |
| Magnesium Stearate | 2.1 g |
| TOTAL | 565.28 g |
| Coated Oxycodone Modified Release Tablets | |
| OPADRY ® WHITE YS-1-18202-A | 20 g |
| Purified water | 80 g |
| Uncoated Oxycodone ER Tablets | 200 g |

Using a coated Oxycodone Resin Complex (that may be prepared as in Example 9) (266.84 g), calcium silicate (RXCIPIENT™ FM 1000) (40.5 g), silicon dioxide (RXCIPIENT™ GL 100) (4.5 g), microcrystalline cellulose (AVICEL® PH 101) (127.74 g), crospovidone (KOLLIDON™ CL-SF) (18 g), lactose monohydrate (FLOWLAC™ 100) (96.6 g), and talc (IMPERIAL™ 500) (9 g) are passed through 40 mesh screen and mixed for 10 minutes using cube blender (ERWEKA™ AR-402). Magnesium stearate (2.1 g) is passed through a 40 mesh screen, added into the blender and further mixed for 5 minutes. The blend is compressed into tablets using rotary tablet press (MINIPRESS™) fitted with a 0.3440×0.7500 capsule shape tooling. Tablets are compressed with weight of 942.14 mg (equivalent to 100 mg morphine sulfate), hardness of 7-11 kp, at machine speed of 5-30 rpm.

A non-functional coating may be prepared and applied as follows. OPADRY®WHITE YS-1-18202-A-20 g is dispersed into purified water (80 g) and mixed for 45 minutes using propeller mixer (ARROW™). The coating process is performed in a perforated coating pan (VECTOR™ LDCS-5) by applying 20 g of coating solution to 200-1 g Oxycodone modified release tablets. The coating conditions are controlled by exhaust temperature of 30° C. and spray rate of 5 g/min.

Example 11

Preparation of Hybrid Coated Opioid Resin Complex Using

Dowex Resin

A coated morphine ion exchange resin complex may be prepared as described in Example 1, using a strongly acidic Dow™ resin in place of the Amberlite™ resin described in Example 1.

| Ingredient | Quantity |
| --- | --- |
| Morphine Ion Resin Complex | |
| Morphine Sulfate | 450 g |
| Purified Water | 5 L |
| DOW XYS-40010.00 | 807 g |
| KOLLICOAT SR-30D polymer system (30% dispersion) | 501 g |
| Hybrid Coated Morphine Ion Resin Complex | |
| KOLLICOAT SR-30D polymer system (30% dispersion) | 693.38 g |
| Triacetin | 10.37 g |
| SURETERIC 90G 18507 White PVAP system | 41.6 g |
| Purified Water | 554.65 g |
| Morphine Ion Resin Complex | 600 g |

A morphine sulfate complex may be prepared by first dissolving 450 g of morphine sulfate in 5 liters of purified water, and then slowly adding 807 g of DOWEX™ resin with continuous mixing. The dispersion is mixed for 1 hour and upon completion, the dispersion is filtered through a filtration apparatus (Buchner funnel) with the aid of vacuum. The dispersion/filtration process is repeated twice with 4800 g of purified water. The wet resin complex is then dried in a VECTOR™ FLM-1 fluid bed processor at 50° C. until moisture content is about 15-25%. KOLLICOAT™ SR-30D of 501 g is then slowly added to the wet resin complex in a Hobart type mixer (Kitchen Aid) to form a uniform mass. The wet mass is again dried at 50° C. in a VECTOR™ FLM-1 fluid bed processor to the moisture content around 20%. The semi dried granules are then milled through a 40 mesh screen using CO-MIL™ brand mill and continued drying at 50° C. until moisture content is about 3-7%. The dried granules are then milled through a 40 mesh screen using CO-MIL™ brand mill [QUADRO].

In a separate container, 10.37 g of triacetin and 693.38 g of KOLLICOAT™ SR-30D are mixed for 1 hour (solution-A). SURETERIC™ 90G 18507 White is dispersed in 554.65 g of purified water and mixed for 30 minutes (solution-B) using propeller mixer (ARROW™). Solution B is added into Solution A and mixed for 1 hour using propeller mixer (ARROW™). The final coating is passed through 40 mesh screen. The coating process is performed in a VECTOR™ FLM-1 fluid bed processor by applying 1,200 g of coating solution to 600 g of Morphine sulfate Complex using WURSTER process that results in 40% weight gain. The coating conditions are controlled at an inlet temperature of 25-35° C., air flow of 10-25 cfm, nozzle pressure of 2-3 kg/cm$^2$, accelerator air pressure of 1 kg/cm$^2$, and spray rate of 2.5-10 g/min so that uniform coating is achieved. The coated morphine resin complex is then placed at 60° C. in VWR™ convection oven for 5 hours.

Example 12

It is desirable to reduce the ability of an abuser to "release" the active drug in a form which is readily injected or otherwise administered to achieve a "high". Thus, the ability to deter immediate release of the drug from the composition of the invention by abuse is desired.

Hybrid Coated Morphine Ion Exchange resin tablets of the invention prepared in Example 2 were assessed for abuse potential. Each of eight beakers contained an amount of hybrid coated morphine ion exchange resin equivalent to 200 mg morphine sulfate, i.e., each contained two tablets prepared as described in Example 2 or ground tablets.

The contents of each beaker were either assessed either "as is" (2 soaked tablets per beaker) or "ground" (prior to the placement in the beaker, tablets were ground and the equivalent of 200 mg morphine sulfate placed in each beaker). For the "ground samples", the tablets were ground in a coffee grinder which is commercially available for home use for one minute [MR. COFFEE® grinder, Model IDS57], resulting in a mixture ranging from powder to granular size.

For each of the "as is" and "ground" tablet samples, the testing involved soaking (i) in water with stirring at room temperature, (ii) in water without stirring at room temperature, (iii) in 40% ethanol solution with stirring at room temperature, (iv) in 40% ethanol solution without stirring at room temperature. For each sample subjected to stirring, the solution was stirred in a VWR 5-position standard multiposition stirrer at a setting of 3.

Release from "as is" or "ground" tablets under each of these conditions was assessed at designated times (10 minutes, 30 minutes, 1 hr, 3 hr, and 6 hr). More particularly, each sample was analyzed for the percentage (%) of morphine in solution using high performance liquid chromatography (HPLC) against a standard of morphine sulfate. The standard consisted of a commercially purchased morphine sulfate, API version. For HPLC, a C18 column was set with the flow rate of 1 mL/min with detector set at 280 nm was used. The mobile phase consists of 20% (v/v) methanol, 0.1% triethylamine (v/v), 0.005M octanesulfonic acid sodium salt, 0.177 M sodium acetate, and pH adjusted to 6.5 with glacial acetic acid.

In the samples subjected to water treatment, the amount of morphine released ranged from 2.0% at 10 minutes to 2.5% at 6 hours (ground, unstirred) and ranged from 2.2% at 10 minutes to 7.3% at 6 hours (ground, stirred). The amount of morphine release in the "as is" samples subjected to water treatment was lower, ranging from 2.9% (10 min) to 5.2% (6 hours) for stirred and ranging from 1.6% (10 minutes) to 0.8% (6 hours) for unstirred.

The sample subjected to grinding and ethanol with stirring showed the highest release of active, ranging from 7.2% of morphine being released at 10 minutes to 14.8% of morphine being released at 6 hours. The sample subjected to grinding and ethanol without stirring showed release ranging from 2.4% morphine release (at 10 minutes) to 5.3% morphine release (6 hours).

The "as is" sample subjected to ethanol solution with stirring showed a release of active ranging from 0.4% (10 minutes) to 5.7% (6 hours); whereas the "as is" sample subjected to ethanol solution without stirring showed a release of active ranging from 0.2% (10 minutes) to 2.3% (6 hours).

As anticipated, these results showed that when soaked intact (i.e., "as is"), the release of morphine is relatively low. However, when subjected to abuse, e.g., by grinding, a higher percentage of morphine release is observed for the tablet of Example 2.

The abuse potential of granules taken from a 100 mg Kadian® extended release capsule was also assessed using the conditions described above. The results of this assessment showed that when the granules from the Kadian® extended release capsule were soaked intact ("as is"), a relatively low release of morphine sulfate was observed, with the exception of soaking in 40% ethanol at 6 hours where a significant release was observed.

The ground granules from the Kadian® capsule showed a significantly greater percentage of morphine sulfate released as compared to amount of active released from the ground tablet of Example 2 (results described above) under the same conditions.

All patents, patent publications, and other publications listed in this specification are incorporated herein by reference. While the invention has been described with reference to a particularly preferred embodiment, it will be appreciated that modifications can be made without departing from the spirit of the invention. Such modifications are intended to fall within the scope of the appended claims.

The invention claimed is:

1. A solid oral dose tablet, powder or granular formulation having modified release characteristics comprising at least one hybrid coated opioid-ion exchange resin complex and pharmaceutically acceptable excipients, said at least one hybrid coated opioid-ion exchange resin complex comprising: a pharmaceutically effective amount of an opioid bound to a pharmaceutically acceptable ion exchange resin; and
 a cured hybrid modified release coating layer over the opioid-ion exchange resin complex, said hybrid coating comprising:
  a pH-independent, high tensile strength, water insoluble, water-permeable, diffusion barrier coating forming component comprising about 70% to about 90% w/w polyvinylacetate (PVA) and about 3 to about 10% w/w of a plasticizer; and
  an enteric coating forming component having pH-dependent solubility in an aqueous system which is non-reactive with said barrier coating forming component, said enteric coating forming component comprising polyvinylacetate phthalate, wherein said barrier coating forming component and said enteric coating forming component are present in a weight ratio of about 20:1 to about 3:1.

2. The solid dose formulation according to claim 1, wherein the opioid is morphine or morphine sulfate.

3. The solid dose formulation according to claim 1, wherein the solid formulation is a tablet.

4. The solid dose formulation according to claim 1, wherein the solid formulation is granules in a capsule.

5. The solid dose formulation according to claim 1, wherein said barrier coating forming component and said enteric coating forming component are present in a ratio of about 6:1 to 4:1 wt/wt.

6. The solid dose formulation according to claim 1, wherein the plasticizer in said barrier coating forming component is selected from the group consisting of dibutyl sebacate, propylene glycol, polyethylene glycol, polyvinyl alcohol, triethyl citrate, acetyl triethyl citrate, acetyl tributyl citrate, tributyl citrate, triacetin, Soluphor P, and mixtures thereof.

7. The solid dose formulation according to claim 6, wherein the plasticizer is triacetin.

8. The solid dose formulation according to claim 1, wherein the hybrid coating comprises 25% to 50% by weight of the complex.

9. The solid dose formulation according to claim 8, wherein the hybrid coating comprises 30% to 45% by weight of the complex.

10. The solid dose formulation according to claim 1, wherein said enteric coating forming component comprises polyvinylacetate phthalate and 10% titanium dioxide.

11. The solid dose formulation according to claim 1, wherein the enteric coating component comprises a polyinylacetate phthalate, at least one plasticizer, and one or more selected from the group consisting of a detackifier, a lubricant, an alkalizing agent, a viscosity modifier, and an anticaking agent.

12. The solid dose formulation according to claim 11, wherein the at least one plasticizer in the enteric coating component comprises a liquid plasticizer and a solid plasticizer.

13. The solid dose formulation according to claim 12, wherein the liquid plasticizer is triethylcitrate.

14. The solid dose formulation according to claim 12, wherein the solid plasticizer is polyethylene glycol 3350.

15. The solid dose formulation according to claim 1, wherein the resin further comprises a release retardant which forms a matrix with the resin complex, wherein said hybrid coating is over said opioid-ion exchange resin complex-matrix.

16. The solid dose formulation according to claim 15 wherein the release retardant is selected from the group consisting of a polyvinyl acetate polymer, ethyl cellulose, cellulose acetate, acrylic based polymers or copolymers, cellulose phthalate, and mixtures thereof.

17. The solid dose formulation according to claim 1, wherein said opioid drug-ion exchange resin complex is in a matrix which further comprises a solvating agent and wherein said hybrid coating is over said opioid-ion exchange resin complex matrix.

18. The solid dose formulation according to claim 17, wherein said hybrid coating is present in an amount which provides a 40% weight gain over the opioid-drug ion exchange resin complex-matrix.

19. The solid dose formulation according to claim 17, wherein the solvating agent is polyvinyl pyrrolidone.

20. The solid dose formulation according to claim 1, wherein the barrier coating forming component comprises PVA, a stabilizer, a surfactant and a plasticizer.

21. The solid dose formulation according to claim 20, wherein the stabilizer is a polyvinylpyrrolidone.

22. The solid dose formulation according to claim 21, wherein the polyvinyl pyrrolidone comprises about 5 to about 10% w/w of the barrier coating component.

23. The solid dose formulation according to claim 20, wherein the surfactant is sodium lauryl sulfate.

24. The solid dose formulation according to claim 1, wherein the opioid drug is selected from the group consisting of opioid analgesics drugs selected from the group consisting of hydrocodone, morphine, hydromorphone, oxycodone, codeine, levorphanol, meperidine, methadone, oxymorphone, buprenorphine, fentanyl, dipipanone, tramadol, etorphine, dihydroetorphine, butorphanol, levorphanol, or salts thereof or mixtures thereof.

25. The solid dose formulation according to claim 20, wherein the opioid is selected from morphine or morphine sulfate.

* * * * *